United States Patent [19]

Block et al.

[11] Patent Number: 4,976,965

[45] Date of Patent: Dec. 11, 1990

[54] CORONARY AFFECTING MEDICINAL COMPOSITION

[75] Inventors: Juergen Block, Schlob Ricklingen; Lutz Feicho, Burgdorf; Alwin Sobe, Sarstedt; Martin Wischniewski, Neustadt/Rbge., all of Fed. Rep. of Germany

[73] Assignee: Kali-Chemie Pharma GmbH, Hanover, Fed. Rep. of Germany

[21] Appl. No.: 91,555

[22] Filed: Aug. 31, 1987

[30] Foreign Application Priority Data

Apr. 30, 1987 [DE] Fed. Rep. of Germany .... 3714402.2

[51] Int. Cl.$^5$ ................................. A61K 9/64
[52] U.S. Cl. ........................................ 424/456; 424/45
[58] Field of Search ................. 424/45, 435, 441, 443, 424/456

[56] References Cited

U.S. PATENT DOCUMENTS

| | | | |
|---|---|---|---|
| 3,155,574 | 11/1964 | Silson et al. | 167/54 |
| 3,579,392 | 5/1971 | Enoksson | 149/7 |
| 3,784,684 | 1/1974 | Bossert et al. | 424/37 |
| 4,439,439 | 3/1984 | Ballany et al. | 424/270 |
| 4,689,233 | 8/1987 | Dvorsky et al. | 424/456 |
| 4,773,907 | 9/1988 | Urguhart et al. | 424/452 |
| 4,794,001 | 12/1988 | Mehta et al. | 424/453 |
| 4,795,643 | 1/1989 | Seth | 424/456 |

FOREIGN PATENT DOCUMENTS

| | | |
|---|---|---|
| 61806 | 10/1982 | European Pat. Off. . |
| 3315805 | 11/1984 | European Pat. Off. . |
| 143857 | 6/1985 | European Pat. Off. . |
| 175671 | 3/1986 | European Pat. Off. . |
| 182635 | 5/1986 | European Pat. Off. . |
| 230226 | 7/1987 | European Pat. Off. . |
| 1808922 | 6/1969 | Fed. Rep. of Germany . |
| 1792448 | 2/1972 | Fed. Rep. of Germany . |
| 65929 | 10/1972 | Luxembourg . |
| 970027 | 9/1964 | United Kingdom . |

*Primary Examiner*—Olik Chaudhuri
*Assistant Examiner*—Andrew Griffis
*Attorney, Agent, or Firm*—Foley, Lardner, Schwartz, Jeffery, Schwaab, Mack, Blumenthal & Evans

[57] ABSTRACT

Coronary affecting medicinal compositions which in addition to a coronary affecting substance selected from the group consisting of isosorbide nitrates and dihydropyridines contain an alkylene glycol ether as a solvent.

9 Claims, No Drawings

CORONARY AFFECTING MEDICINAL COMPOSITION

BACKGROUND OF THE INVENTION

The present invention relates to a medicinal composition containing a coronary activity affecting substance and an alkylene glycol ether.

One medicinal composition of this type is already known from British Patent No. GB-A 970,027. Aerosol preparations containing nitroglycerin as a coronary affecting substance are described therein which contain the active substance dissolved in a lower alcohol in combination with a propellant or a propellant mixture. For safety reasons, so that no explosive concentration of nitroglycerin can occur when the easily volatile solvent or propellant evaporates, a phlegmatizing agent selected from the group of polyalkylene glycols and their derivatives is added to the mixture. Included among a broad listing of phlegmatizing agents are monoalkyl ethers of polyalkylene glycols, but polyalkylene glycols are preferably utilized. Further, in all of the actual embodiments, the proportion of phlegmatizing agent is always less than 10 percent by weight with respect to the mixture containing the active substance.

Other medicinal compositions are known from European Patent Application EP-A No. 0,143,857, according to which soft gelatine capsules contain a filling of the coronary affecting substance nifedipine dissolved in a mixture of a tetrahydrofurfuryl alcohol-polyethylene glycol ether (THFP) and polyvinyl pyrrolidone (PVP). The proportion of the essential component PVP in the actual examples comprises at least 13% by weight of the filling of the capsule. This formulation thereby overcomes disadvantages of solid nifedipine formulations which contain insoluble crosslinked PVP (PVPP), but they are subject to the limitation that they must include large amounts of a supplemental adjuvant in the filling of the capsule.

SUMMARY OF THE INVENTION

It is therefore the object of the present invention to make available new medicinal compositions containing coronary affecting substances.

It is a particular object of the invention to provide compositions which from the point of view of their composition are simply constituted and which are subject to as few limitations as possible.

These and other objects of the invention are achieved by providing a medicinal composition comprising a mixture of an effective coronary activity affecting amount of a coronary activity affecting active substance selected from the group consisting of isosorbide nitrates and dihydropyridines, and an alkylene glycol ether corresponding to the formula $XO(RO)_nH$ in which X represents $C_1$ to $C_4$ alkyl, R represents $CH_2-CH_2$ and n is 2.

DETAILED DESCRIPTION OF THE PREFERRED EMBODIMENTS

The medicinal formulations of the invention are characterized in that they contain a coronary activity affecting substance selected from the group isosorbide nitrates or dihydropyridines together with an alkylene glycol ether corresponding to the formula:

$$XO(RO)_nH$$

in which
X represents an alkyl group having 1 to 4 carbon atoms;
R represents $CH_2-CH_2$; and
n represents 2.

In particular, the alkyl groups may include methyl, ethyl, n-propyl, i-propyl or n-butyl groups. Preferably the alkyl group is ethyl.

In accordance with the invention, the proportion of alkylene glycol ether in the active substance-containing mixture ranges from greater than 10 to 99% by weight. Preferably the proportion of alkylene glycol ether is from 30 to 99% by weight.

In one embodiment of the invention the active substance may be a known isosorbide nitrate compound. In particular, the isosorbide nitrate may be isosorbide-5-mononitrate (1,4:3,6-dianhydrosorbitol-5-mononitrate) or isosorbide-2,5-dinitrate (1,4:3,6-dianhydrosorbitol-2,5-dinitrate).

A further embodiment of the invention envisions use of known dihydropyridine derivatives as active substances. Nicardipine (1,4-dihydro-2,6-dimethyl-4-(3-nitrophenyl)-3,5-pyridine-dicarboxylic acid methyl 2-[methyl-(phenylmethyl)amino]ethyl ester and nifedipine (1,4-dihydro-2,6-dimethyl-4-(2-nitrophenyl)-3,5-pyridinedicarboxylic acid dimethyl ester) may be mentioned as illustrative examples of such dihydropyridine compounds.

In the broadest formulation of the invention the mixture of active substance and alkylene glycol ether constitutes the completed medicinal composition. This mixture is simply produced by dissolving the active substance in the alkylene glycol ether, whereby, in contrast to the prior art solutions (for example, solutions of nifedipine in viscous media such polyethylene glycol, polyethylene glycol/glycerin, etc.) no heating is required during the dissolving operation. Clear solutions are obtained which can be compounded or confected in the usual manner, for example in dropper bottles, ampules, etc. In the case of nifedipine as the active substance, care must be taken thereby to assure sufficient protection against light.

In appropriate circumstances conventional formulation adjuvants can be added to the solutions. One group of adjuvants are, for example, known perfumes (aroma agents), etheric oils, menthol, sweeteners.

Due to the excellent solvent characteristic of the alkylene glycol ether it is further possible to incorporate other pharmaceutically acceptable solvents such as, for example, polyols, particularly diols or triols, and monoalcohols, particularly ethanol. These solvents are preferably utilized in amounts from 1 to 15% by weight with respect to the total mixture. The solution is even stable against addition of certain amounts of water without precipitation or separation of the active substance occurring.

In cases in which a more viscous preparation of the active substance is desired, this can be achieved by adding known polymeric binders which for the most part exhibit excellent compatibility with the alkylene glycol ether.

Other possible additives include those which influence the hydrophilic-lipophilic behavior of the solution of active substance. Such adjuvants may, for example, be glycerides, such as monoglycerides or diglycerides. Preferably, they are triglycerides of fatty acids with 8 to 12 carbon atoms. These adjuvants may be used in place of from 1 to 50% by weight of the alkylene glycol ether.

In one particular embodiment of the invention the solutions, optionally modified by addition of adjuvants, are filled into spray bottles and are used as inhalation sprays or, preferably, as sublingual sprays. Their low viscosity makes the solutions according to the invention particularly suitable for use in pump spray bottles since they can be sprayed readily and uniformly. It is, however, also possible to fill the solutions into known types of spray containers driven by propellant gas.

Another particular embodiment of the invention envisions that the solutions, optionally modified by addition of adjuvants, are filled in a known manner into soft gelatine capsules, preferably chewable gelatine capsules. For this purpose the solutions are encapsulated with an aqueous gel of gelatine and softener, for example according to the Scherer process, and dried. Suitable softeners include polyols such a glycerin or polyethylene glycol. In these cases it may be advantageous to already incorporate a small proportion of softener in the solution to be encapsulated in order to avoid later brittleness or cracking of the capsule shells.

In combination with the formulation of the invention it has been found to be advantageous to utilize sorbitol or similar polyols, particularly oligomers of glycerin, preferably diglycerin or triglycerin, as softeners. Corresponding capsules do not necessary require a separate addition of softener in the filling and are very stable. These softeners are utilized in amounts of about 4 to 40% by weight with respect to the total weight of the finished capsule shells. If nifedipine is utilized as the active substance, then the capsule shells should be provided in a known manner with protection against light. In its simplest form this can take place by providing the capsule with a light-impervious covering.

It is also possible, however, to make the capsules themselves light-impervious in any known manner. This can, for example, be achieved by incorporation of soluble dyes which absorb in the ultraviolet and short wave visible light portions of the spectrum and/or by inclusion of colored or colorless pigments. Soluble dyes can also be added directly to the solution of active substance in one embodiment of the invention.

The solutions according to the invention can be produced very simply and easily and, as previously explained, can either be further processed directly or used as starting compositions for various formulations.

The following examples will serve to further characterize the invention without limiting its scope.

EXAMPLE 1

To produce soft gelatine capsules 2.0 g glycerine (85% solution) were added to a starting composition of 6.25 g nifedipine and 91.75 g diethylene glycol monoethyl ether (DME). This solution was filled into size 1.3 (minims) soft gelatine capsules according to the Scherer process. Even after storage for one year these capsules showed no changes such as brittleness, cracking, etc.

In an analagous manner capsules were produced with fillings having the following recipes (in parts by weight):

|  | 1a | 1b | 1c |
|---|---|---|---|
| Nefedipine | 5.0 | 10.0 | 10.0 |
| DME | 103.5 | 170.3 | 207.0 |
| Glycerin (85%) | 6.5 | 3.7 | 13.0 |
| Water | 6.5 | — | 13.0 |
| Na-saccharine | 0.15 | — | 0.3 |

-continued

|  | 1a | 1b | 1c |
|---|---|---|---|
| Menthol | 0.35 | — | 0.7 |
| Capsule size (minims) | 2 | 3 | 4 |

In capsule 1b diglycerine was utilized in place of glycerine both in the filling and also in the capsule wall. The capsule wall was provided with light protection by addition of titanium dioxide and iron oxide brown.

EXAMPLE 2

The following ingredients (indicated in parts by weight) were filled into pump aerosol bottles with dosing valves (one push=0.06 ml):

|  | 2a | 2b |
|---|---|---|
| Nifedipine | 8.4 | — |
| Isosorbide mononitrate | — | 2.0 |
| DME | 91.25 | 48.83 |
| Neutral oil* | — | 48.82 |
| Menthol | 0.25 | 0.25 |
| Na-saccharine | 0.1 | 0.1 |

*mixture of triglycerides of $C_8$-$C_{12}$ fatty acids.

The foregoing description and examples have been set forth merely to illustrate the invention and are not intended to be limiting. Since modifications of the described embodiments incorporating the spirit and substance of the invention may occur to persons skilled in the art, the scope of the invention should be limited solely with respect to the appended claims and equivalents.

What is claimed is:

1. A medicinal composition for administration through the mouth, said composition being selected from the group consisting of chewable gelatine capsules and sublingual sprays and comprising a mixture of an effective coronary activity affecting amount of a coronary activity affecting active substance selected from the group consisting of isosorbide nitrates and dihydropyridines, and at least 10% by weight of an alkylene glycol ether corresponding to the formula $XO(RO)_nH$ in which X represents $C_1$ to $C_4$ alkyl, R represents $CH_2$-$CH_2$ and n is 2, wherein said composition is essentially free of polyvinylpyrrolidone (PVP).

2. A medicinal composition according to claim 1, wherein the proportion of alkylene glycol ether amounts to from more than 10 to 99 % by weight relative to the total weight of the active substancecontaining mixture.

3. A medicinal composition according to claim 2, wherein the proportion of alkylene glycol ether amounts to form 30 to 99 % by weight relative to the total weight of the active substancecontaining mixture.

4. A medicinal composition according to claim 1, wherein the active substance is isosorbide mononitrate or dinitrate.

5. A medicinal composition according to claim 1, wherein the active substance is a dihydropyridine compound.

6. A medicinal composition according to claim 5, wherein the active substance is nifedipine.

7. A chewable gelatine capsule containing a filling according to claim 1.

8. A chewable capsule according to claim 7, wherein said capsule has a gelatine shell which is light-impervious.

9. A sublingual spray comprising a medicinal composition according to claim 1.

* * * * *